United States Patent
Zabic et al.

(10) Patent No.: US 11,335,038 B2
(45) Date of Patent: May 17, 2022

(54) SYSTEM AND METHOD FOR COMPUTED TOMOGRAPHIC IMAGING

(71) Applicant: UIH AMERICA, INC., Houston, TX (US)

(72) Inventors: Stanislav Zabic, Houston, TX (US); Patrick Joseph Kling, Houston, TX (US)

(73) Assignee: UIH AMERICA, INC., Houston, TX (US)

( * ) Notice: Subject to any disclaimer, the term of this patent is extended or adjusted under 35 U.S.C. 154(b) by 206 days.

(21) Appl. No.: 16/673,856

(22) Filed: Nov. 4, 2019

(65) Prior Publication Data

US 2021/0134026 A1    May 6, 2021

(51) Int. Cl.
| | |
|---|---|
| *G06K 9/00* | (2022.01) |
| *G06T 11/00* | (2006.01) |
| *G06T 7/73* | (2017.01) |
| *A61B 6/03* | (2006.01) |
| *A61B 6/00* | (2006.01) |
| *G01N 23/046* | (2018.01) |

(52) U.S. Cl.
CPC ............ *G06T 11/005* (2013.01); *A61B 6/032* (2013.01); *A61B 6/4233* (2013.01); *G01N 23/046* (2013.01); *G06T 7/74* (2017.01); *G06T 11/006* (2013.01); *G01N 2223/413* (2013.01); *G01N 2223/42* (2013.01); *G06T 2207/10081* (2013.01); *G06T 2207/30004* (2013.01); *G06T 2210/21* (2013.01); *G06T 2210/41* (2013.01)

(58) Field of Classification Search
CPC .................................................... G06T 11/005
See application file for complete search history.

(56) References Cited

U.S. PATENT DOCUMENTS

| | | | |
|---|---|---|---|
| 8,913,805 B2 | 12/2014 | Long et al. | |
| 2013/0343672 A1* | 12/2013 | Yu | G06T 11/003 382/276 |
| 2015/0213630 A1* | 7/2015 | Szirmay-Kalos | G06T 1/20 382/131 |
| 2017/0135659 A1* | 5/2017 | Wang | A61B 6/5258 |
| 2020/0294285 A1* | 9/2020 | Song | G06T 5/50 |
| 2020/0294289 A1* | 9/2020 | Entezari | G16H 30/40 |

OTHER PUBLICATIONS

Long et al 3D Forward and Back-Projection for X-Ray CT Using Separable Footprints, IEEE (Year: 2010).*

(Continued)

*Primary Examiner* — Oneal R Mistry
(74) *Attorney, Agent, or Firm* — Metis IP LLC

(57) ABSTRACT

The present disclosure directs to a system and method for CT imaging. The method may include acquiring computed tomography (CT) data, wherein the CT data is generated by scanning a subject using a CT scanner, the CT scanner including a focal spot and a detector, and the detector including a plurality of detector units. The method may also include obtaining a forward projection model and a back projection model, wherein the forward projection model and the back projection model are associated with sizes of the detector units and a size of the focal spot of the CT scanner. The method may further include reconstructing a CT image of the subject iteratively based on the CT data, the forward projection model, and the back projection model.

20 Claims, 9 Drawing Sheets

(56) References Cited

OTHER PUBLICATIONS

Levakhina "Chapter 3 Forward and Back Projection Model" Springer (Year: 2014).*

Joseph, P. M., An improved Algorithm for Reprojecting Rays Through Pixel Images, IEEE Transactions on Medical Imaging, 1(3): 192-196, 1982.

Siddon, R. L., Fast Calculation of the Exact Radiological Path Length for a Three-Dimensional CT Array, Medical Physics, 12(2): 252-255, 1985.

Kohler, TH. et al., Efficient Forward Projection Through Discrete Data Sets Using Tri-Linear Interpolation, IEEE Nuclear Science Symposium, 2. 113-115, 2000.

* cited by examiner

SYSTEM AND METHOD FOR COMPUTED TOMOGRAPHIC IMAGING

TECHNICAL FIELD

The present disclosure generally relates to medical imaging, and more particularly to a system and method for model-based iterative computed tomographic (CT) imaging.

BACKGROUND

Computed tomography (CT) is a technology that makes use of computer-processed combinations of X-ray images taken from different angles to produce cross-sectional images. The CT technology has been widely used in medical diagnosis, for example, human body imaging. However, conventional model-based iterative CT reconstruction techniques used in CT imaging may be inaccurate because the sizes of a detector element and/or a focal spot of a CT scanner are not taken into account. Thus, there is a need for a system and method for reconstructing a CT image more accurately by considering the finite sizes of the detector element and the focal spot.

SUMMARY

In a first aspect of the present disclosure, a method is provided. The method may be implemented on a computing apparatus having at least one processor and at least one computer-readable storage device. The method may include acquiring computed tomography (CT) data, wherein the CT data is generated by scanning a subject using a CT scanner, the CT scanner including a focal spot and a detector, and the detector including a plurality of detector units; obtaining a forward projection model and a back projection model, wherein the forward projection model and the back projection model are associated with sizes of the detector units and a size of the focal spot of the CT scanner; and reconstructing a CT image of the subject iteratively based on the CT data, the forward projection model, and the back projection model.

In a second aspect of the present disclosure, a system is provided. The system may include at least one storage medium including a set of instructions, and at least one processor in communication with the at least one storage medium. When executing the set of instructions, the at least one processor may be configured to direct the system to perform operations including acquiring computed tomography (CT) data, wherein the CT data is generated by scanning a subject using a CT scanner, the CT scanner including a focal spot and a detector, and the detector including a plurality of detector units; obtaining a forward projection model and a back projection model, wherein the forward projection model and the back projection model are associated with sizes of the detector units and a size of the focal spot of the CT scanner; and reconstructing a CT image of the subject iteratively based on the CT data, the forward projection model, and the back projection model.

In a third aspect of the present disclosure, a non-transitory computer readable medium may store instructions, the instructions, when executed by at least one processor, the at least one processor may be configured to perform operations including acquiring computed tomography (CT) data, wherein the CT data is generated by scanning a subject using a CT scanner, the CT scanner including a focal spot and a detector, and the detector including a plurality of detector units; obtaining a forward projection model and a back projection model, wherein the forward projection model and the back projection model are associated with sizes of the detector units and a size of the focal spot of the CT scanner; and reconstructing a CT image of the subject iteratively based on the CT data, the forward projection model, and the back projection model.

In some embodiments, the obtaining a forward projection model and a back projection model may include, for each detector element of the plurality of detector elements, setting a detector plane representing the detector unit and a focal spot plane representing the focal spot in a three dimensional (3D) space; setting a plurality of voxels representing the subject between the detector plane and the focal spot plane; sampling a first count points on the detector plane and a second count of points on the focal spot plane; determining a set of lines, each of the set of lines connecting a sampled detector point with a sampled focal spot point; determining intersection points of the set of lines with surfaces of the plurality of voxels; ranking the intersection points on each line; and determining, based on the ranked intersection points on each line, the forward projection model and the back projection model of the each line.

In some embodiments, the detector plane may include at least four first boundary points, and the focal spot plane may include at least four second boundary points.

In some embodiments, the sampling a first count of first points on the detector plane and a second count of second points on the focal spot plane may include determining boundaries of the detector plane and boundaries of the focal spot plane based on the at least four boundary points on each plane; sampling a first portion of the first count of first points on the boundaries of the detector plane; sampling a first portion of the second count of second points on the boundaries of the focal spot plane; meshing the detector plane according to the first portion of first points; meshing the focal spot plane according to the first portion of second points; sampling a second portion of the first count of first points based on the meshed detector plane; and sampling a second portion of the second count of second points based on the meshed focal spot plane.

In some embodiments, the meshed focal spot plane includes a plurality of grids, and each grid of the plurality of grids corresponds to a weight with respect to the entire focal spot plane.

In some embodiments, the method may further include optimizing the forward projection model and the back projection model based on the weight of each grid on the focal spot plane.

In some embodiments, the ranking the determined intersection points on each line may include determining a coordinate difference between a first point on the detector plane and a second point on the focal spot plane on the each line, the coordinate difference including an x-component and a y-component; obtaining a determination result by determining whether the x-component is greater than the y-component; and ranking, based on the determination result, the intersection points on the each line.

In some embodiments, the determination result is that the x-component is greater than the y-component, and the ranking, based on the determination result, the intersection points may include ranking the intersection points on the each line in an ascending order according to x-components of the intersection points.

In some embodiments, the determination result is that the x-component is smaller than the y-component, and the ranking, based on the determination result, the intersection points may include ranking the determined intersection points on the each line in an ascending order according to y-components of the intersection points.

In some embodiments, the determining the forward projection model based on the ranked intersection points on the each line may include, for each line, determining an absolute norm of each two sequential intersection points of the ranked intersection points of the each line; determining, based on coordinates of the each two sequential intersection points, a voxel coordinate of each voxel corresponding to the each two sequential intersection points; determining first contribution of the plurality of voxels on the line based on the voxel coordinates and the absolute norms associated with the each line; and determining the forward projection model based on the first contribution of the plurality of voxels on the each line.

In some embodiments, the determining the forward projection model based on the first contribution of the plurality of voxels on the each line may include determining a total contribution by summing, regarding the set of lines, the first contribution of the plurality of voxels on the each line; and averaging the total contribution by the count of the set of lines.

In some embodiments, the determining the back projection model based on the ranked intersection points may include determining second contribution of each line on the plurality of voxels based on the absolute norms associated with the each line; and determining the back projection model based on the second contribution of each line on the plurality of voxels and the forward projection model.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
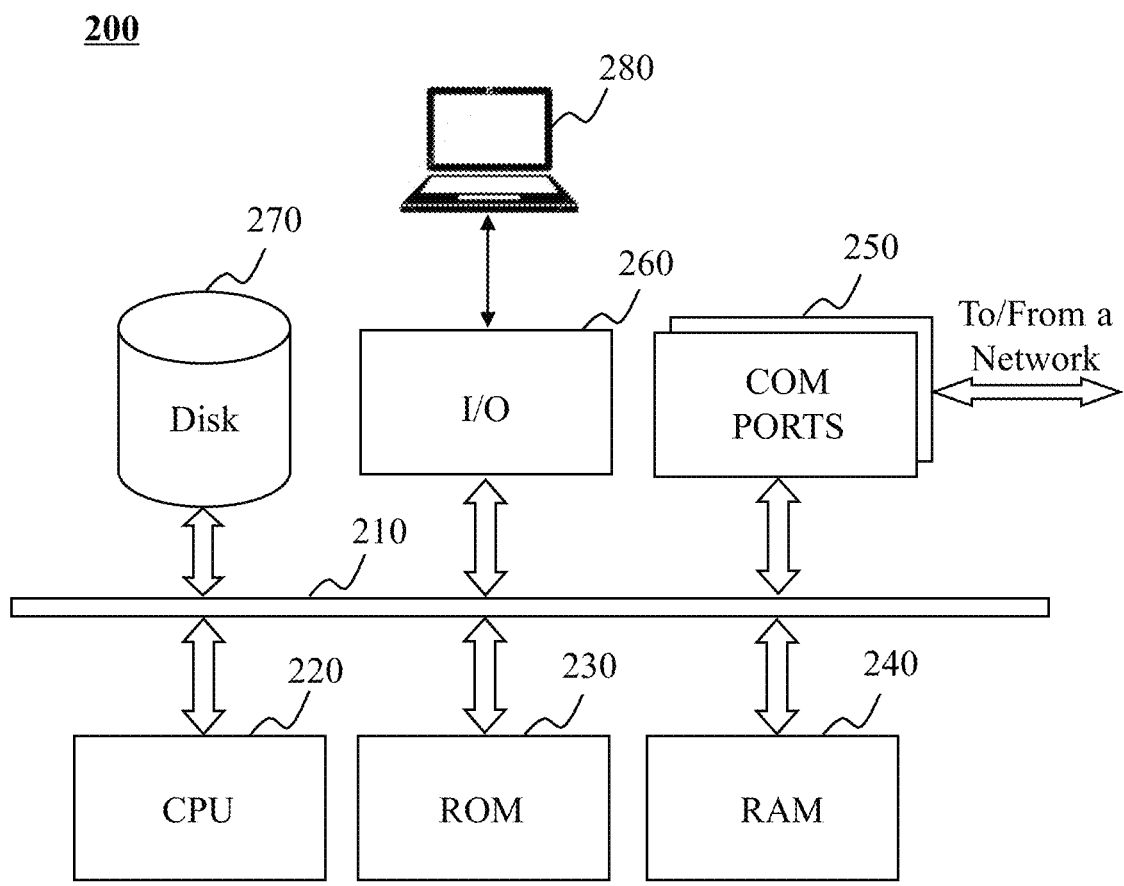
FIG. 2 is a schematic diagram illustrating exemplary components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for non-invasive imaging, such as for disease diagnosis, treatment, and/or research purposes. In some embodiments, the imaging system may be a computed tomography (CT) system, a magnetic resonance imaging (MRI) system, a computed tomography-positron emission tomography (CT-PET) system, an emission computed tomography (ECT) system, a computed tomography-magnetic resonance imaging (CT-MRI) system, an ultrasonography system, an X-ray photography system, or the like, or any combination thereof.

For illustration purposes, the disclosure is directed to systems and methods for model-based iterative CT image reconstruction (MBIR). Forward projection model and the back projection model considering finite sizes of detector elements and focal spot shapes and positions in a CT scanner may be used in the MBIR so as to improve the accuracy of reconstructed CT images.

Figure 1:
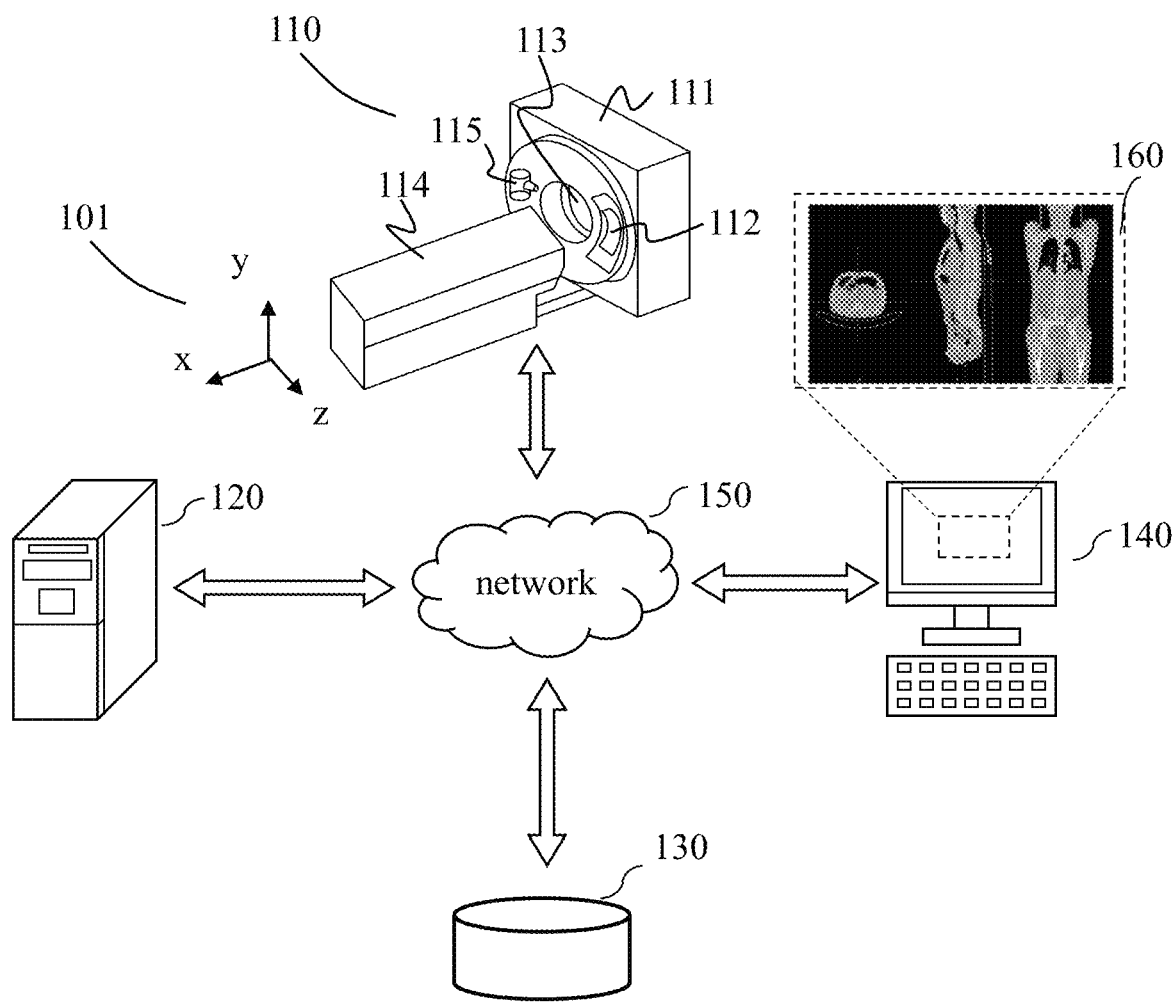
FIG. 1 is a schematic diagram illustrating an exemplary imaging system 100 according to some embodiments of the present disclosure.

FIG. 1 is a schematic diagram illustrating an exemplary imaging system 100 according to some embodiments of the present disclosure. The imaging system 100 may include a CT scanner 110, a processing apparatus 120, a storage device 130, a terminal device 140, and a network 150.

The CT scanner 110 may include a gantry 111, a detector 112, a detecting region 113, a table 114, and a radiation source 115. The gantry 111 may support the detector 112 and the radiation source 115. A subject (e.g., a patient) may be placed on the table 114 for CT scanning. The radiation source 115 may emit x-rays. The x-rays are emitted from a focal spot using a high-intensity magnetic field to form an x-ray beam. The x-ray beam may travel toward the subject. The detector 112 may detect x-ray photons from the detecting region 113. In some embodiments, the detector 112 may include one or more detector units. The detector unit(s) may be and/or include single-row detector elements and/or multi-row detector elements.

The apparatus 120 may process data and/or information acquired from the CT scanner 110, or retrieved from, e.g., the storage device 130, the terminal device 140, and/or an external device (external relative to the system 100) via the network 150. For example, the processing apparatus 120 may determine a forward projection model and a back projection model taking in consideration of the sizes of the detector elements of the detector 112 and the shape and size of the focal spot, and reconstruct a CT image iteratively based on the forward projection model and the back projection model. In some embodiments, the processing apparatus 120 may be a computer, a user console, a single server, a server group, etc. The server group may be centralized or distributed. In some embodiments, the processing apparatus 120 may be local or remote. For example, the processing apparatus 120 may access information and/or data stored in the CT scanner 110, the terminal device 140, and/or the storage device 130 via the network 150. As another example, the processing apparatus 120 may be directly connected to the CT scanner 110, the terminal device 140, and/or the storage device 130 to access stored information and/or data. In some embodiments, the processing apparatus 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing apparatus 120 may be implemented by a computing device 200 having one or more components as illustrated in FIG. 2.

The storage device 130 may store data, instructions, and/or any other information. In some embodiments, the storage device 130 may store data obtained from the CT scanner 110, the terminal device 140, and/or the processing apparatus 120. In some embodiments, the storage device 130 may store data and/or instructions that the processing apparatus 120 may execute or use to perform exemplary methods described in the present disclosure. In some embodiments, the storage device 130 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the imaging system 100 (e.g., the processing apparatus 120, the terminal device 140, etc.). One or more components in the imaging system 100 may access the data or instructions stored in the storage device 130 via the network 150. In some embodiments, the storage device 130 may be directly connected to or communicate with one or more other components in the imaging system 100 (e.g., the processing apparatus 120, the terminal device 140, etc.). In some embodiments, the storage device 130 may be part of the processing apparatus 120.

The terminal device 140 may input/output signals, data, information, etc. In some embodiments, the terminal device 140 may enable a user interaction with the processing apparatus 120. For example, the terminal device 140 may display a reconstructed CT image on a screen 160. As another example, the terminal device 140 may obtain a user's input information through an input device (e.g., a keyboard, a touch screen, a brain wave monitoring device, etc.), and transmit the input information to the processing apparatus 120 for further processing. The terminal device 140 may be a desktop computer, a tablet computer, a laptop computer, a mobile device, or the like, or any combination thereof. In some embodiments, the mobile device may include a home device, a wearable device, a mobile device, a virtual reality device, an augmented reality device, or the like, or any combination thereof. In some embodiments, the home device may include a lighting device, a control device of an intelligent electrical apparatus, a monitoring device, a television, a video camera, an interphone, or the like, or any combination thereof. In some embodiments, the wearable device may include a bracelet, a footgear, eyeglasses, a helmet, a watch, clothing, a backpack, an accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™ an Oculus Rift™, a Hololens™, a Gear VR™, etc. In some embodiments, the terminal device 140 may be part of the processing apparatus 120 or a peripheral device of the processing apparatus 120 (e.g., a console connected to and/or communicating with the processing apparatus 120).

The network 150 may include any suitable network that can facilitate the exchange of information and/or data for the imaging system 100. In some embodiments, one or more components of the imaging system 100 (e.g., the CT scanner 110, the terminal device 140, the processing apparatus 120, the storage device 130, etc.) may communicate information and/or data with one or more other components of the imaging system 100 via the network 150. For example, the processing apparatus 120 may obtain CT data from the CT scanner 110 via the network 150. As another example, the processing apparatus 120 may obtain user instructions from the terminal device 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network, 4G network, 5G network), a frame relay network, a virtual private network (VPN), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected to the network 150 to exchange data and/or information.

FIG. 2 is a schematic diagram illustrating exemplary components of a computing device according to some embodiments of the present disclosure. The CT scanner 110, the processing apparatus 120, the storage device 130, and/or the terminal device 140 may be implemented on the computing device 200 according to some embodiments of the present disclosure. The particular system may use a functional block diagram to explain the hardware platform containing one or more user interfaces. The computing device may be a computer with general or specific functions. Both types of the computers may be configured to implement any particular system according to some embodiments of the present disclosure. The computing device 200 may be configured to implement any components that perform one or more functions disclosed in the present disclosure. For example, the computing device 200 may implement any component of the imaging system 100 as described herein. In FIGS. 1 and 2, only one such computer device is shown purely for convenience purposes. One of ordinarily skilled in the art would have understood at the time of filing of this application that the computer functions relating to the imaging as described herein may be implemented in a distributed fashion on a number of similar platforms, to distribute the processing load.

The computing device 200, for example, may include COM ports 250 connected to and from a network connected thereto to facilitate data communications. The computing device 200 may also include a processor (e.g., the central processing unit (CPU) 220), in the form of one or more processors (e.g., logic circuits), for executing program instructions. For example, the processor may include interface circuits and processing circuits therein. The interface circuits may be configured to receive electronic signals from a bus 210, wherein the electronic signals encode structured data and/or instructions for the processing circuits to process. The processing circuits may conduct logic calculations, and then determine a conclusion, a result, and/or an instruction encoded as electronic signals. Then the interface circuits may send out the electronic signals from the processing circuits via the bus 210.

The exemplary computing device may include the internal communication bus 210, program storage and data storage of different forms including, for example, a disk 270, and a read only memory (ROM) 230, or a random access memory (RAM) 240, for various data files to be processed and/or transmitted by the computing device. The exemplary computing device may also include program instructions stored in the ROM 230, RAM 240, and/or another type of non-transitory storage medium to be executed by the CPU 220. The methods and/or processes of the present disclosure may be implemented as the program instructions. The computing device 200 also includes an I/O component 260, supporting input/output between the computer 280 and other components. The computing device 200 may also receive programming and data via network communications.

Merely for illustration, only one processor and/or processor is illustrated in FIG. 2. Multiple CPUs and/or processors are also contemplated; and thus, operations and/or method steps performed by one CPU and/or processor as described in the present disclosure may also be jointly or separately performed by the multiple CPUs and/or processors. For example, if in the present disclosure the CPU and/or processor of the computing device 200 executes both operation A and operation B, it should be understood that operation A and operation B may also be performed by two different CPUs and/or processors jointly or separately in the computing device 200 (e.g., the first processor executes operation A and the second processor executes operation B, or the first and second processors jointly execute operations A and B).

Figure 3:
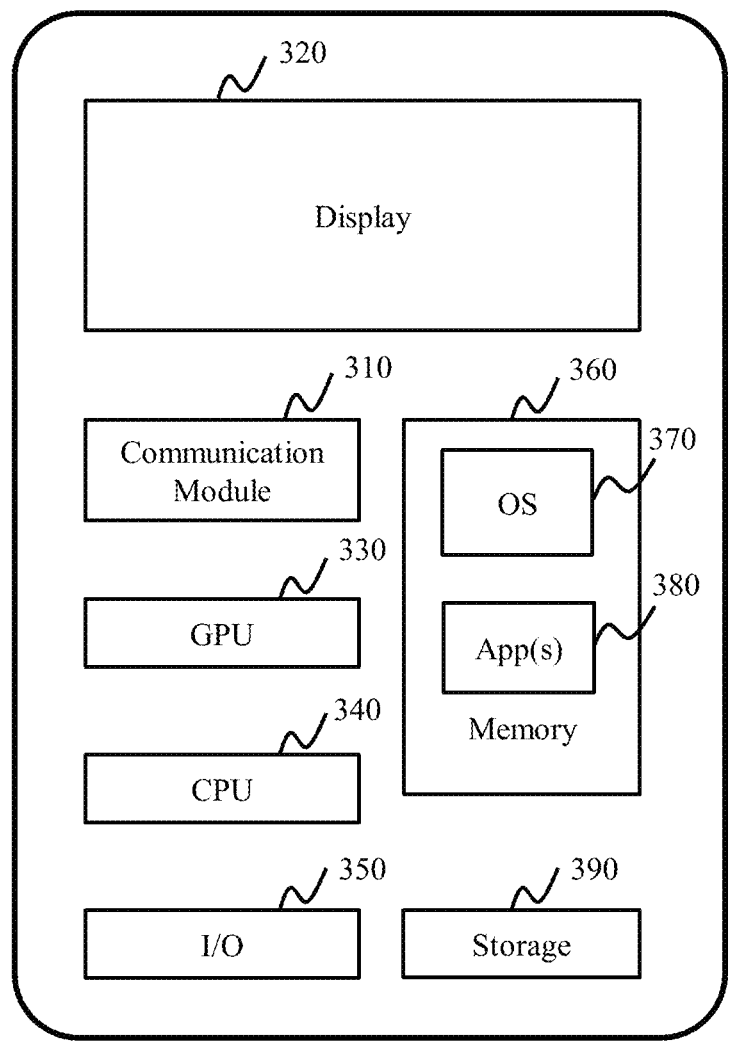
FIG. 3 is a block diagram illustrating exemplary hardware and/or software components of an exemplary mobile device according to some embodiments of the present disclosure.

FIG. 3 is a block diagram illustrating exemplary hardware and/or software components of an exemplary mobile device according to some embodiments of the present disclosure. The processing apparatus 120 or the terminal device 140 may be implemented on the mobile device 300 according to some embodiments of the present disclosure. As illustrated in FIG. 3, the mobile device 300 may include a communication module 310, a display 320, a graphics processing unit (GPU) 330, a central processing unit (CPU) 340, an I/O 350, a memory 360, and storage 390. The CPU 340 may include interface circuits and processing circuits similar to the CPU 220. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to CT imaging from the imaging system on the mobile device 300. User interactions with the information stream may be achieved via the I/O devices 350 and provided to the processing apparatus 120 and/or other components of the imaging system 100 via the network 150.

In order to implement various modules, units and their functions described above, a computer may be used as hardware platforms of one or more elements (e.g., a component of the processing apparatus 120 described in FIG. 1). Since these hardware elements, operating systems, and program languages are common, it may be assumed that persons skilled in the art may be familiar with these techniques and they may be able to provide information required in the data classification according to the techniques described in the present disclosure. A computer with a user interface may be used as a personal computer (PC), or other types of workstations or terminal devices. After being properly programmed, a computer with a user interface may be used as a server. It may be considered that those skilled in the art may also be familiar with such structures, programs, or general operations of this type of computer device. Thus, additional explanations are not described for the figures.

Figure 4:
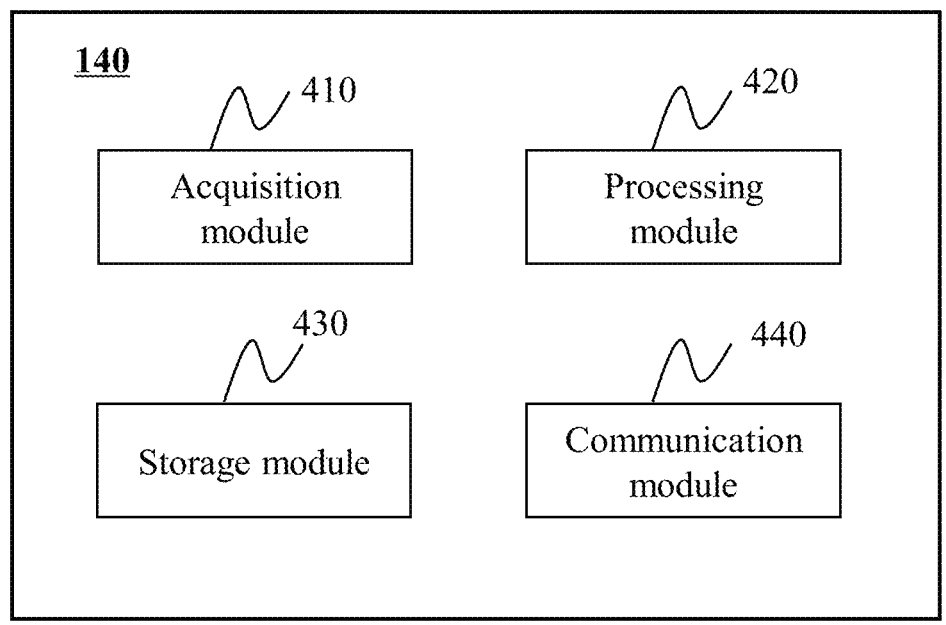
FIG. 4 is a block diagram illustrating an exemplary processing apparatus according to some embodiments of the present disclosure.

FIG. 4 is a block diagram illustrating an exemplary processing apparatus 120 according to some embodiments of the present disclosure. As illustrated in FIG. 4, the processing apparatus 120 may include an acquisition module 410, a processing module 420, a storage module 430, and a communication module 440.

The acquisition module 410 may acquire data. The acquisition module 410 may acquire data from the CT scanner 110, the storage device 130, the terminal device 140, or any devices or components capable of storing data via the network 150. For example, the acquisition module 410 may acquire data from a medical cloud data center (not shown) via the network 150. The acquired data may include CT data, processing results (e.g., processed CT data, CT images), user instructions, algorithms, program codes, or the like, or a combination thereof. In some embodiments, the acquisition module 410 may acquire CT data from the CT scanner 110, more particularly, from the CT detector 112. The CT data may be generated by scanning the subject using a CT scanner (e.g., the CT scanner 110). Merely for illustration purposes, the subject may be placed on the table 114, and the CT scanner 110 may acquire CT data by scanning the subject in a predetermined scanning mode (e.g., spiral scanning). The CT data may relate to the intensity of x-rays that pass through the subject and are detected by the detector 112. The acquisition module 410 may transmit the acquired data to a storage device (e.g., the storage module 430, the storage device 130, etc.) for storage. The CT data may be stored in the form of voxel information, images, vectors, or the like, or any combination thereof. In some embodiments, the acquisition module 410 may transmit the acquired data to a computing device (e.g., the processing module 420) for processing.

The processing module 420 may process data provided by various modules or components of the imaging system 100. For example, the processing module 420 may process CT data acquired by the acquisition module 410, or retrieved from the storage module 430, etc. The processing module 420 may process the obtained data by performing a plurality of operations. Exemplary data processing operations may include data correction, data conversion, forward projection model determination, back projection model determination, image reconstruction, etc. In some embodiments, the processing module 420 may determine a forward projection model and a back projection model, and reconstruct a CT image, using an iterative reconstruction technique, based on the forward projection model, the back projection model, and the acquired CT data.

The storage module 430 may store data. Merely by ways of example, the storage module 430 may store acquired CT data, processed CT data, control parameters, data processing algorithms, or the like, or a combination thereof. In some embodiments, the storage module 430 may store one or more programs and/or instructions that may be executed by the processor(s) of the processing apparatus 120 to perform exemplary methods described in this disclosure. For example, the storage module 430 may store a program for the processing apparatus 120 to reconstruct a CT image of a subject.

The storage module 430 may be or include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc.

The communication module 440 may be connected to a network (e.g., the network 150) to facilitate data communication. The communication module 440 may establish connections between the processing apparatus 120 and the CT scanner 110, storage device 130 and/or the terminal device 140, etc. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication module 440 may be and/or include a standardized communication port, such as RS232, RS485, etc. In some embodiments, the communication module 440 may be a specially designed communication port. For example, the communication module 440 may be designed in accordance with the digital imaging and communications in medicine (DICOM) protocol.

It should be noted that the above description of the processing apparatus 120 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, one or more modules illustrated in FIG. 4 may be implemented in at least part of the exemplary imaging system 100 as illustrated in FIG. 1. For example, the acquisition module 410, the processing module 420, the storage module 430, and/or the communication module 440 may be integrated into a console (not shown). Via the console, a user may set parameters for scanning a subject, controlling imaging processes, correcting CT data, controlling parameters for reconstruction of an image, viewing reconstructed images, etc.

Figure 5:
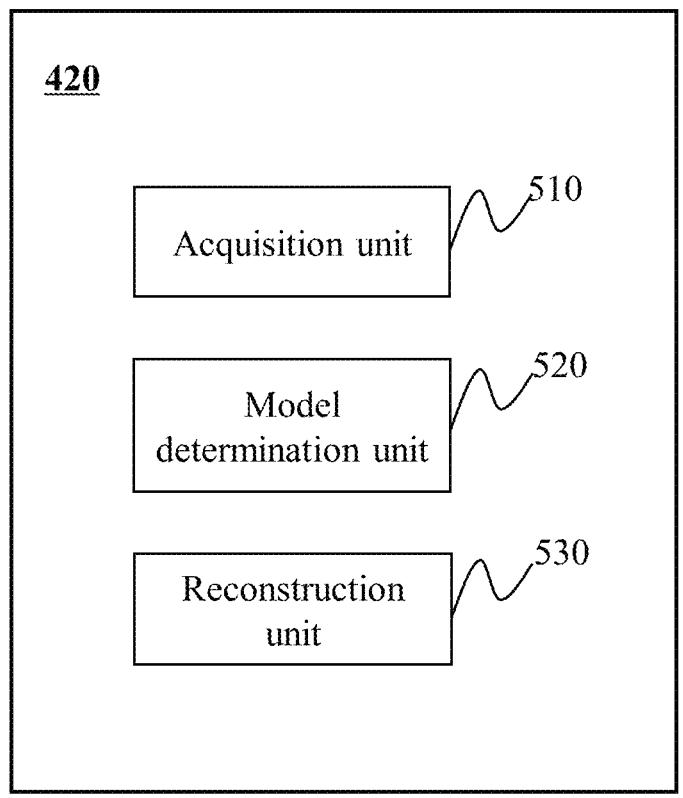
FIG. 5 is a block diagram illustrating an exemplary processing module according to some embodiments of the present disclosure.

FIG. 5 is a block diagram illustrating an exemplary processing module 420 according to some embodiments of the present disclosure. The processing module 420 may include an acquisition unit 510, a model determination unit 520, and a reconstruction unit 530. The one or more units in the processing module 420 may be implemented on various components (e.g., the CPU 220 of the computing device 200 as illustrated in FIG. 2) in the present disclosure.

The acquisition unit 510 may obtain CT data. In some embodiments, the acquisition unit 510 may acquire CT data from a storage device (e.g., the storage device 130, the disk 270, the storage 390, etc.) capable of storing data in the imaging system 100. In some embodiments, the acquisition unit 510 may acquire CT data from a detector (e.g., the detector 112) configured to detect x-rays. The subject may be a patient, a phantom, or the like, or a combination thereof.

The CT data may be generated by scanning the subject using a CT scanner (e.g., the CT scanner 110). Merely for illustration purposes, the subject may be placed on the table 114, and the CT scanner 110 may generate CT data by scanning the subject in a predetermined scanning mode (e.g., spiral scanning). The CT data may relate to the intensity of x-rays that pass through the subject and are detected by the detector 112.

In some embodiments, the acquisition unit 510 may pre-preprocess acquired CT data. For example, the CT data may be pre-processed to removing artifacts (e.g., a signal of the table 114 supporting a subject). As another example, the CT data may be converted into images.

The model determination unit 520 may determine a forward projection model and a back projection model. The forward projection model and the back projection model may be determined by taking into account sizes of detector elements of the detector 112 and the shape and size of a focal spot formed during the CT scan.

In some embodiments, the model determination unit 520 may perform one or more of the following operations to determine the forward projection model and/or the back projection model. Merely for illustration purposes, a detector plane representing a detector element of the detector 112 and a focal spot plane representing the focal spot may be set in a three dimensional (3D) space. A plurality of voxels representing the subject may be set between the detector plane and the focal spot plane. A first count of points may be sampled on the detector plane and a second count of points may be sampled on the focal spot plane. As used herein, a first point refers to a point on the detector plane, and a second point refers to a point on the focal spot plane. A set of lines, each of which connects a sampled first point with a sampled second point may be determined. Intersection points of the set of lines with surfaces of the plurality of voxels may be determined. The determined intersection points on each line may be ranked in a preset order. Then the forward projection model and the back projection model associated with the sizes of detector elements of the detector 112 and the size of the focal spot may be determined based on the ranked intersection points on each line.

The reconstruction unit 530 may reconstruct a CT image of the subject. The reconstruction unit 530 may obtain the acquired CT data from the acquisition unit 510 and the determined forward projection model and the back projection model from the model determination unit 520, and reconstruct the CT image of the subject iteratively based on the acquired CT data, the forward projection model, and the back projection model. In some embodiments, the reconstruction unit 530 may reconstruct the CT image of the subject using an MBIR technique. MBIR may use various models of one or more characteristics of radiation as well as characteristics of the CT scanner. MBIR may use forward projection and back projections to match the reconstructed image to the acquired CT data iteratively according to a metric. The forward projection model and the back projection model may be used in the MBIR so as to reconstruct a CT image.

The iterative reconstruction process may terminate when a preset condition is satisfied. In some embodiments, the preset condition may relate to a difference between two reconstructed images that when the difference is smaller than a preset threshold, the iterative process may terminate. In some embodiments, the preset condition may include a maximum or threshold number (or count) of iterations (for example, one hundred times) to be performed, and when the threshold number (or count) of iterations (or referred to as a threshold iteration count) are performed (i.e., the preset condition is satisfied), the iterative process may terminate. The threshold iteration count may be set by a user, according to default settings of imaging system 100, etc. A CT image obtained when the iterative process terminates may be designated as the reconstructed CT image. The reconstruction unit 530 may transmit the reconstructed CT image to one or more other components of the system 100, e.g., the terminal device 140, the mobile device 300, etc., for display, storage, further processing, or the like, or a combination hereof.

It should be noted that the above description of the processing module 420 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, at least one of the plurality of units in the processing module 420 may include a storage unit (not shown). As another example, any one of the plurality of units in the processing module 420 may be divided into two or more sub-units or blocks. As a further example, the model determination unit 520 may be omitted from the processing module 420. For instance, the forward projection model and/or the back projection model may be determined by the manufacturer of the CT scanner or a third party, and provided or pre-stored in a storage device for future use in image reconstruction. The forward projection model and/or back projection model may be determined using data acquired using a phantom or a subject (or a patient). The forward projection model and/or the back projection model may be updated from time to time or periodically based on data associated with or acquired by the CT scanner on the processing apparatus 120 or on a different processing apparatus that is part of or external to the system 100. In some embodiments, a plurality of forward projection models and/or the back projection models may be provided for a same CT scanner to allow a user to select. Such different forward projection models and/or back projection models may be generated based on different setting of the boundary points on either one of the detector plane or the focal spot plane, different meshing of the detector plane and/or focal spot plane of a same CT scanner, or the like, or a combination thereof.

Figure 6:
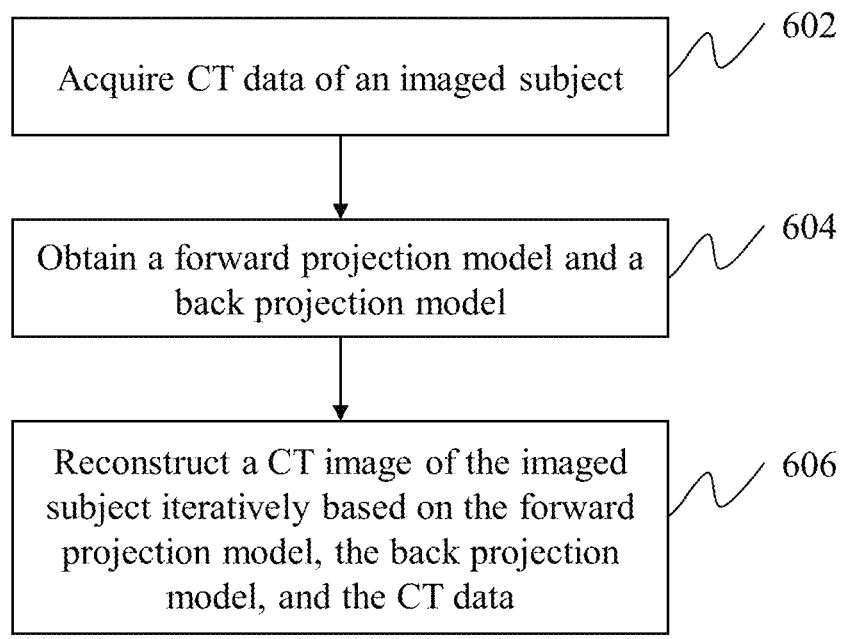
FIG. 6 is a flowchart illustrating an exemplary process for reconstructing a CT image of a subject according to some embodiments of the present disclosure.

FIG. 6 is a flowchart illustrating an exemplary process for reconstructing a CT image of a subject according to some embodiments of the present disclosure. In some embodiments, the process 600 may be executed by the processing module 420. For example, the process 600 may be implemented as a set of instructions stored in the storage device 130, and/or the storage module 430. The processing apparatus 120 and/or the CPU 220 may execute the set of instructions and may accordingly be directed to perform the process 600.

In 602, CT data of a subject may be acquired. The CT data may be acquired by, for example, the acquisition unit 510. In some embodiments, the CT data may be acquired from a storage device (e.g., the storage device 130, the disk 270, the storage 390, etc.) capable of storing data in the imaging system 100. In some embodiments, the CT data may be acquired from a detector (e.g., the detector 112) configured to detect x-rays. The subject may be a patient, a phantom, or the like, or a combination thereof.

The CT data may be generated by scanning the subject using a CT scanner (e.g., the CT scanner 110). Merely for illustration purposes, the subject may be placed on the table 114, and the CT scanner 110 may generate CT data by scanning the subject in a predetermined scanning mode (e.g., spiral scanning). The CT data may relate to the intensity of x-rays that arrive at the detector after passing through the subject. The attenuated x-rays may be detected by the detector 112 and transmitted to the acquisition unit 510. In some embodiments, the CT scanner may include a focal spot and a detector including one or more detector elements. The emitted x-rays may be focused to a focal spot using a high-intensity magnetic field to form an x-ray beam. The detector 112 may detect x-rays impinging thereon, including those passing through the subject. In some embodiments, the detector 112 may include a plurality of detector elements. The plurality of detector elements may be arranged in a single row (referred to as single-row detector elements) and/or multiple rows (referred to as multi-row detector elements).

In some embodiments, the acquired CT data may be transmitted to the storage module 430 to be stored. In some embodiments, the plurality of CT data may be transmitted, in a data flow, to a designated device or component, for example, the processing apparatus 120 of the imaging system 100 or a work station (not shown) connected to the imaging system 100 via the network 150.

In 604, a forward projection model and a back projection model may be obtained. In some embodiments, the forward projection model and the back projection model may be obtained from the model determination unit 520. In some embodiments, the forward projection model and the back projection model may be retrieved from a storage device. The forward projection model and the back projection model may be determined by taking into account the sizes of the detector elements and the shape and size of the focal spot formed when the CT scanner 110 scans the subject. More descriptions regarding the determination of the forward projection model and the back projection model may be found elsewhere in the present disclosure, for example, FIG. 7 and the descriptions thereof.

In 606, a CT image of the subject may be reconstructed iteratively based on the forward projection model, the back projection model, and the CT data. The CT image may be reconstructed by, for example, the reconstruction unit 530. In some embodiments, the CT image of the subject may be reconstructed using an iterative reconstruction technique. Exemplary iterative reconstruction techniques may include but not limited to MBIR, algebraic reconstruction, statistical reconstruction, learned iterative reconstruction, etc. In some embodiments, the CT image of the subject may be reconstructed using an MBIR technique. The MBIR may use various models of one or more characteristics of the CT scanner. The MBIR may use forward projection and back projections to match the reconstructed image to the acquired CT data iteratively according to a metric. The forward projection model and the back projection model may be used in the MBIR so as to reconstruct a CT image.

The iterative reconstruction process may terminate when a preset condition is satisfied. In some embodiments, the preset condition may relate to a difference between two reconstructed images that when the difference is smaller than a preset threshold, the iterative process may terminate. In some embodiments, the preset condition may include a maximum or threshold number (or count) of iterations (for example, one hundred times) to be performed, and when the threshold number (or count) of iterations (or referred to as a threshold iteration count) are performed (i.e., the preset condition is satisfied), the iterative process may terminate. The preset iteration count may be set by a user, according to default settings of imaging system 100, etc. A CT image obtained when the iterative process terminates may be designated as the reconstructed CT image. The reconstructed CT image may be transmitted to one or more other components of the system 100, e.g., the terminal device 140, the mobile device 300, etc., for display, storage, further processing, or the like, or a combination hereof.

It should be noted that the above description of the process 600 is provided for the purposes of illustration, not intended to limit the scope of the present disclosure. For persons having ordinary skills in the art, multiple variations and modifications may be reduced to practice in the light of the present disclosure. For example, the process 600 may further include an operation for storing the CT image of the subject. However, these variations and modifications fall in the scope of the present disclosure.

Figure 7:
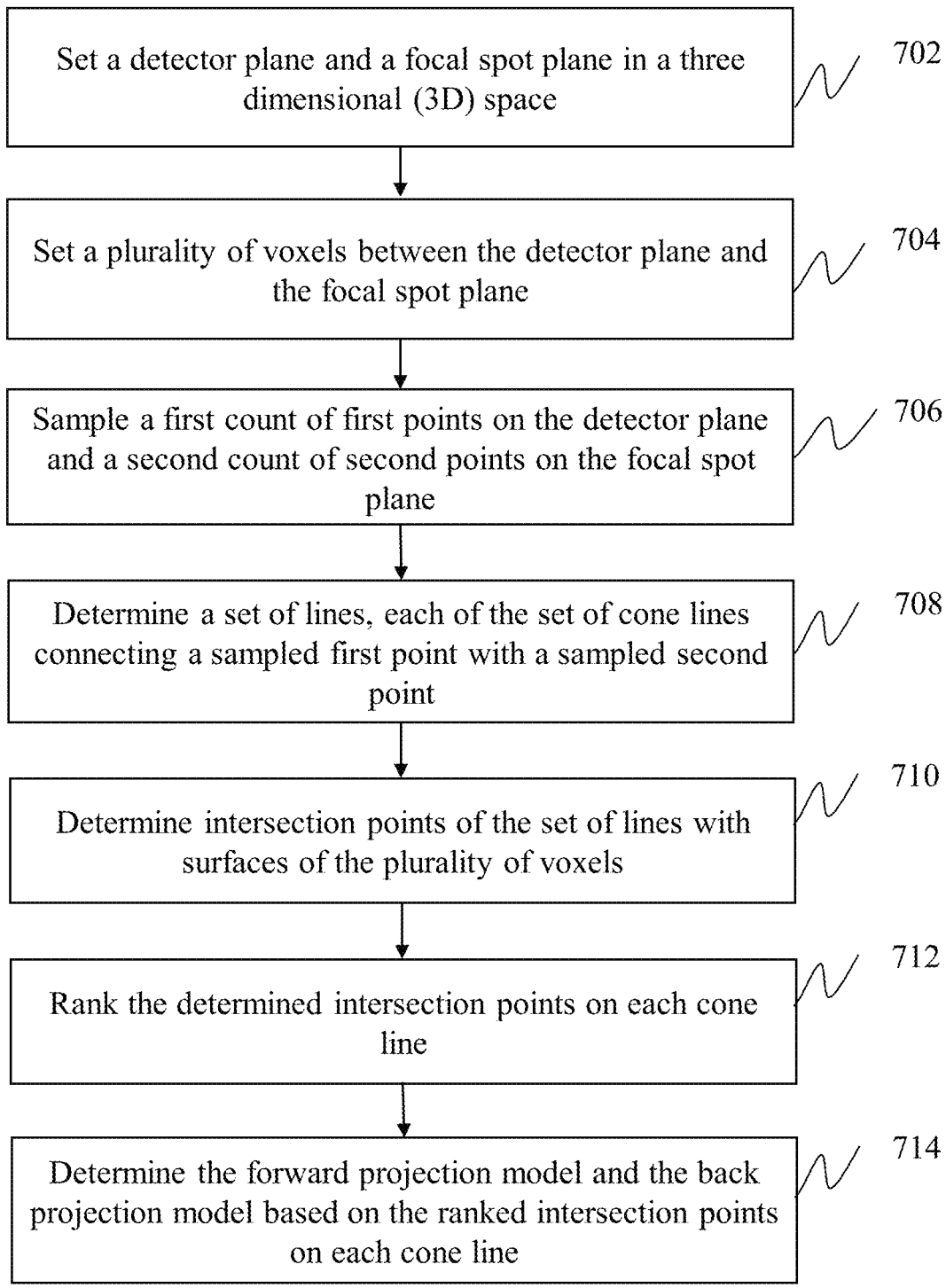
FIG. 7 is a flowchart illustrating an exemplary process for determining a forward projection model and a back projection model according to some embodiments of the present disclosure.

FIG. 7 is a flowchart illustrating an exemplary process for determining a forward projection model and a back projection model according to some embodiments of the present disclosure. In some embodiments, the process 700 may be executed by the processing module 420. For example, the process 700 may be implemented as a set of instructions stored in the storage device 130, and/or the storage module 430. The processing apparatus 120 and/or the CPU 220 may execute the set of instructions and may accordingly be directed to perform the process 700. In some embodiments, the forward projection model and the back projection model referred to in 620 may be determined according to the process 700. The operations 702 through 714 may be performed by the model determination unit 520. In some embodiments, the operations 702 through 714 in the process 700 may be performed with respect to each detector element of a plurality of detector elements.

In 702, a detector plane and a focal spot plane may be set in a three dimensional (3D) space. The detector plane may represent a detector element of a particular size. For example, the detector plane may have the same size and/or the same shape as the detector element. The detector plane may be the area of the detector element where x-rays impinge. In some embodiments, the detector plane may have a shape of a polygon (e.g., a quadrangle, a pentagon, a star-shaped polygon, etc.). The polygon may include at least four first boundary points (i.e., vertexes). As used herein, a first boundary point refers to a point on the boundary of the detector plane. First boundaries (i.e., sides) of the polygon may be straight lines connecting two adjacent first boundary points. As used herein, a first boundary refers to a boundary of the detector plane. As used herein, two first boundary points are considered adjacent to each other if there is no other first boundary point in between. Merely for illustration purposes, the detector plane may be a quadrangle including four first boundary points $\vec{d}_1$, $\vec{d}_2$, $\vec{d}_3$, and $\vec{d}_4$. As used herein, $\vec{d}_1$, $\vec{d}_2$, $\vec{d}_3$, and $\vec{d}_4$ may denote coordinates of the four first boundary points, respectively, in the coordinate system 101 illustrated in FIG. 1. In the coordinate system 101, the x axis is along the direction in which the table 114 moves to transport a subject into or out of the bore of the CT scanner 110 (referred to as the x direction for brevity), the y axis is along the vertical direction pointing from the floor to the ceiling (referred to as the y direction for brevity), and the z axis is along the horizontal direction pointing from the center of the bore of the CT scanner to the side (referred to as the z direction for brevity), and the y direction and the z direction define a plane perpendicular to the x direction. It is understood that the coordinate system 101 is provided here for the purposes of illustration and convenient reference, and is not intended to limit the scope of the present disclosure. A different coordinate system may be employed in implementing the systems and methods disclosed herein.

Figure 9:
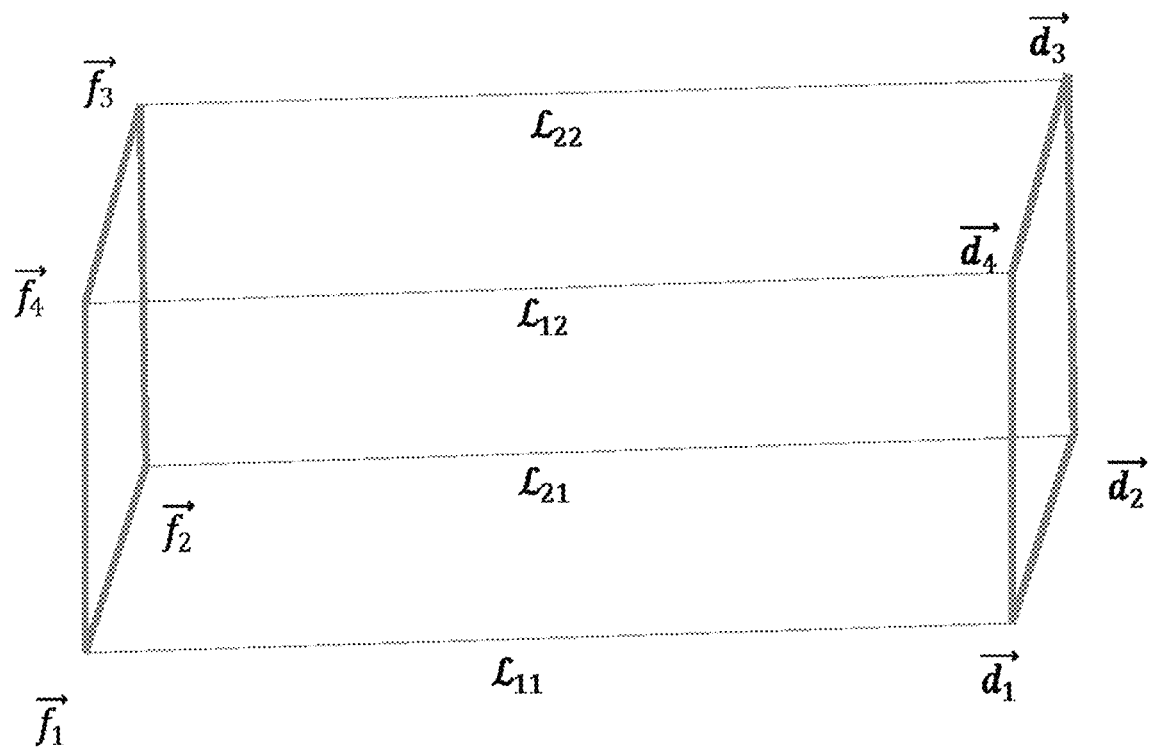
FIG. 9 is a schematic diagram illustrating lines connecting first points on a detector plane with second points on a focal spot plane.

The four first boundary points $\vec{d}_1$, $\vec{d}_2$, $\vec{d}_3$, and $\vec{d}_4$ may be arranged in sequence, e.g., clockwise, as illustrated in FIG. 9. First boundaries of the detector plane may be determined by connecting adjacent first boundary points of the four first boundary points $\vec{d}_1$, $\vec{d}_2$, $\vec{d}_3$, and $\vec{d}_4$. The quadrangle may be a square, a rectangle, a rhombus, etc.

The focal spot plane may represent a focal spot (e.g., the focal spot formed in the CT scanner 110 when the subject is scanned) of a particular size. The focal spot plane may be the area of the detector element where x-rays traverse. For example, the focal spot plane may have a same size and/or a same shape as the focal spot. In some embodiments, the focal spot plane may have a shape of a polygon (e.g., a quadrangle, a pentagon, a star-shaped polygon, etc.). The polygon may include at least four second boundary points. As used herein, a second boundary point refers to a point on the boundary of the focal spot plane. Second boundaries of the polygon may be straight lines connecting two adjacent second boundary points. As used herein, a second boundary refers to a boundary of the focal spot plan. As used herein, two second boundary points are considered adjacent to each other if there is no other second boundary point in between. Merely for illustration purposes, the focal spot plane may be a quadrangle including four second boundary points $\vec{f}_1$, $\vec{f}_2$, $\vec{f}_3$, and $\vec{f}_4$. As used herein, $\vec{f}_1$, $\vec{f}_2$, $\vec{f}_3$, and $f_4$ may denote coordinates of the four second boundary points, respectively, in the coordinate system 101 illustrated in FIG. 1. The four second boundary points $\vec{f}_1$, $\vec{f}_2$, $\vec{f}_3$, and $\vec{f}_4$. may be in sequence, for example, clockwise as illustrated in FIG. 9. Second boundaries of the focal spot plane may be determined by connecting adjacent second boundary points of the four second boundary points $\vec{f}_1$, $\vec{f}_2$, $\vec{f}_3$, and $\vec{f}_4$. The quadrangle may be a square, a rectangle, a rhombus, etc.

In some embodiments, the detector plane and the focal spot plane may be set to be parallel to each other in the 3D space. The distance between the detector plane and the focal spot plane may be determined by a user, according to default settings of the imaging system 100, etc. In some embodiment, the distance between the detector plane and the focal spot plane may be equal to an actual distance between the detector element and the focal spot in the CT scanner when the subject is scanned.

In 704, a plurality of voxels may be set between the detector plane and the focal spot plane. The plurality of voxels may represent a subject (e.g., the subject scanned by the CT scanner 110). For example, the volume of the plurality of voxels may be the same as or close to the volume of the subject in the pathway of the x-rays emitted from the focal spot of the CT scanner 110. Each voxel may have a particular volume. The volume of the plurality of voxels herein may refer to a sum of the volume of each voxel. In some embodiments, each voxel may have a same size and/or shape. For example, each voxel may have the shape of a cube. In some embodiments, the volume of each voxel may be set by a user, according to default settings of the imaging system 100, etc.

Merely for illustration purposes, the size of each voxel may be $\Delta_x \times \Delta_y \times \Delta_z$, where $\Delta_x$ denotes the length of the voxel, $\Delta_y$ denotes the height of the voxel, and $\Delta_z$ denotes the width of the voxel. The center of the plurality of voxels may be represented by $(D_x, D_y, D_z)$, where $D_x$ denotes the x-coordinate of the center of the voxel, $D_y$ denotes the y-coordinate of the center of the voxel, and $D_z$ denotes the z-coordinate of the center of the voxel. The number (or count) of voxels may be represented by $M_x \times M_y \times M_z$, where $M_x$ denotes the number (or count) of voxels in the x direction, $M_y$ denotes the number (or count) of voxels in the y direction, and $M_z$ denotes the number (or count) of voxels in the z direction.

In some embodiments, the plurality of voxels may be arranged in a grid-shaped structure. The grid-shaped structure may include a plurality of grid planes for separating each voxel apart from neighboring voxels. In some embodiments, grid planes separating a voxel apart from neighboring voxels may be on a same plane (i.e., coplanar) as surfaces of the voxel (also referred to as voxel surfaces). Merely for illustration purposes, voxel surfaces of cubical voxels (voxels each having the shape of a cube) may be represented in formulas (1)-(6):

$$S_{xk} = \{(x,y,z) | x = x_k, y > -D_y, y < M_y \Delta_y - D_y, z > -D_z, z < M_z \Delta_z - D_z\}, \quad (1)$$

$$S_{yl} = \{(x,y,z) | y = y_l, x > -D_x, x < M_x \Delta_x - D_x, z > -D_z, z < M_z \Delta_z - D_z\}, \quad (2)$$

$$S_{zn} = \{(x,y,z) | z = z_n, x > -D_x, y < M_x \Delta_x - D_x, y > -D_y, y < M_y \Delta_y - D_y\}, \quad (3)$$

$$x_k = k \Delta_x - D_x, \quad (4)$$

$$y_l = l \Delta_y - D_y, \quad (5)$$

$$z_n = n \Delta_z - D_z, \quad (6)$$

where $S_{xk}$ denotes voxel surfaces perpendicular to the x axis, $S_{yl}$ denotes voxel surfaces perpendicular to the y axis of the coordinate system 101, $S_{zn}$ denotes voxel surfaces perpendicular to the z axis of the coordinate system 101, $x_k$ denotes intersection points of the voxel surfaces $S_{xk}$ and the x axis of the coordinate system 101, $y_l$ denotes intersection points of the voxel surfaces $S_{yl}$ and the y axis, $z_n$ denotes intersection points of the voxel surfaces $S_{zn}$ and the z axis, k denotes a natural number from 0 to $M_x$, l denotes a natural number from 0 to $M_y$, and n denotes a natural number from 0 to $M_z$.

In some embodiments, the positions of the plurality of voxels may be determined according to the position of the subject. For example, the distance between the focal spot plane and a center of the voxels may be equal to or close to the distance between the focal spot and a center of the subject, and the distance between the center of the voxels and the detector plane may be equal to or close to the distance between the center of the subject and the detector element.

In 706, a first count of points may be sampled on the detector plane and a second count of points may be sampled on the focal spot plane. In some embodiments, first boundaries of the detector plane may be determined based on the at least four boundary points of the detector plane. The first boundaries of the detector plane may be straight lines connecting two sequential boundary points.

The first count of first points may include a first portion of the first count of first points (also referred to as the first portion of first points for brevity) and a second portion of the first count of first points (also referred to as the second portion of first points for brevity). In some embodiments, the first portion of first points may be sampled on the first boundaries. For example, one or more equally distanced points may be sampled on each of the first boundaries. The one or more equally distanced points on each first boundary and the at least three first boundary points of the detector plane may be sampled and designated as the first portion of first points. The second portion of first points may be sampled in an inside portion of the detector plane, not on the first boundaries. In some embodiments, the detector plane may be meshed based on the first portion of first points. The second portion of first points may be sampled based on the meshed detector plane. For example, the detector plane may be meshed by connecting equally distanced points on one boundary with corresponding equally distanced points on another boundary on the opposite side. As used herein, a point A on a boundary A of the first boundaries is considered to correspond to a point B on a boundary B of the first boundaries that is opposite to the boundary A if, viewed from the same direction (e.g., from below $\overrightarrow{d_1 d_2}$ toward $\overrightarrow{d_1 d_2}$ and $\overrightarrow{d_3 d_4}$ as illustrated in FIG. 9, or from above $\overrightarrow{d_3 d_4}$ toward $\overrightarrow{d_1 d_2}$ and $\overrightarrow{d_3 d_4}$ as illustrated in FIG. 9), the point A and the point B are positioned similarly among the points on their respective boundaries. For instance, when viewed from the same direction, a point on the left-most of the boundary A is considered corresponding to a point on the left-most of the boundary B, and a point on the right-most of the boundary A is considered corresponding to a point on the right-most of the boundary B. The points formed in the detector plane when the detector plane is meshed may be sampled as the second portion of first points. For instance, when the detector plane is meshed using two groups of straight lines in which straight lines of each group are parallel to each other, and one group of straight lines are perpendicular to the other group of straight lines, the points formed in the detector plane may refer to those where the two groups of straight lines cross each other.

Similarly, boundaries of the focal spot plane may be determined based on the at least four boundary points of the focal spot plane. The second boundaries of the focal spot plane may be straight lines connecting two adjacent boundary points.

The second count of second points may include a first portion of the second count of second points (also referred to as the first portion of second points for brevity) and a second portion of the second count of second points (also referred to as the second portion of second points for brevity). In some embodiments, the first portion of second points may be sampled on the second boundaries. For example, one or more equally distanced points may be sampled on each of the second boundaries. The one or more equally distanced points on each second boundary and the at least three second boundary points of the focal spot plane may be sampled and designated as the first portion of second points. The second portion of second points may be sampled in an inside portion of the focal spot plane, not on the second boundaries. In some embodiments, the focal spot plane may be meshed based on the first portion of second points. The second portion of second points may be sampled based on the meshed focal spot plane. For example, the focal spot plane may also be meshed by connecting equally distanced points on one boundary with corresponding equally distanced points on another boundary on the opposite side. As used herein, a point C on a boundary C of the second boundaries is considered to correspond to a point D on a boundary D of the second boundaries that is opposite to the boundary C if, viewed from the same direction (e.g., For example, from below $\overrightarrow{f_1 f_2}$ toward $\overrightarrow{f_1 f_2}$ and $\overrightarrow{f_3 f_4}$ as illustrated in FIG. 9, or from above $\overrightarrow{f_3 f_4}$ toward $\overrightarrow{f_1 f_2}$ and $\overrightarrow{f_3 f_4}$ as illustrated in FIG. 9), the point C and the point D are positioned similarly among the points on their respective boundaries. For instance, when viewed from the same direction, a point on the left-most of the boundary C is considered corresponding to a point on the left-most of the boundary D, and a point on the right-most of the boundary C is considered corresponding to a point on the right-most of the boundary D. The points formed in the focal spot plane when the focal spot plane is meshed may be sampled as the second portion of second points. For instance, when the focal spot plane is meshed using two groups of straight lines in which straight lines of each group are parallel to each other, and one group of straight lines are perpendicular to the other group of straight lines, the points formed in the focal spot plane may refer to those where the two groups of straight lines cross each other.

Figure 8:
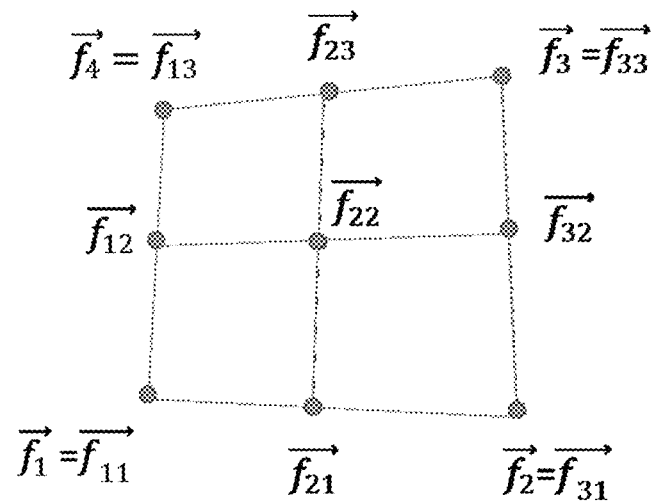
FIG. 8 is a schematic diagram illustrating a second count of second points sampled on the focal spot plane.

Merely for illustration purposes, a second count of second points may be sampled on the focal spot plane as illustrated in FIG. 8. The focal spot plane may be a quadrangle including four second boundary points $\vec{f_1}$, $\vec{f_2}$, $\vec{f_3}$, and $\vec{f_4}$. Four boundaries of a quadrangle representing the focal spot plane may be straight lines. $N_x$ points ($N_x \geq 2$) may be sampled on a boundary in a direction $\vec{f_2}-\vec{f_1}$, and $N_y$ points ($N_y \geq 2$) may be sampled on a boundary in a direction $\vec{f_4}-\vec{f_1}$. In some embodiments, $N_x$ and $N_y$ may be set by a user, according to default settings of the imaging system 100, etc. As shown in FIG. 8, three points ($N_x=3$, $N_y=3$) including the boundary points may be sampled on each second boundary. The focal spot plane may be meshed into four parts based on the sampled points. One or more points formed in the focal spot plane when the focal spot plane is meshed may also be sampled. The sampled points (also referred to as samples) on the focal spot plane may include $\vec{f_{11}}$, $\vec{f_{21}}$, $\vec{f_{31}}$, $\vec{f_{32}}$, $\vec{f_{33}}$, $\vec{f_{23}}$, $\vec{f_{13}}$, $\vec{f_{12}}$, and $\vec{f_{22}}$. Coordinates of the sampled second points on the focal spot plane may be determined according to Formula (7):

$$\vec{f_{i,j}} = \frac{(N_y - j)\left((N_x - i)\vec{f_1} + (i - 1)\vec{f_2}\right) + (j - 1)\left((N_x - i)\vec{f_4} + (i - 1)\vec{f_3}\right)}{(N_x - 1)(N_y - 1)}, \quad (7)$$

where $\vec{f_{i,j}}$ denotes a coordinate of a sampled point, $\vec{f_1}$, $\vec{f_2}$, $\vec{f_3}$, and $\vec{f_4}$ denote boundary points of the focal spot, $N_x$ denotes points sampled on a boundary in a direction $\vec{f_2}-\vec{f_1}$, $N_y$ denotes points sampled on a boundary in a direction $\vec{f_4}-\vec{f_1}$, i denotes an integer ranging from 1 to $N_x$, and j denotes an integer ranging from 1 to $N_y$. Similarly, coordinates of sampled first points on the detector plane may be determined according to Formula (8):

$$\vec{d_{i,j}} = \frac{(N_y - j)\left((N_x - i)\vec{d_1} + (i - 1)\vec{d_2}\right) + (j - 1)\left((N_x - i)\vec{d_4} + (i - 1)\vec{d_3}\right)}{(N_x - 1)(N_y - 1)}, \quad (8)$$

where $\vec{d_{i,j}}$ denotes a coordinate of a sampled first point, and $\vec{d_1}$, $\vec{d_2}$, $\vec{d_3}$, and $\vec{d_4}$ denote first boundary points.

In 708, a set of cone lines may be determined, each of the set of cone lines connecting a sampled first point with a corresponding sampled second point. Referring to FIG. 9, lines connect samples on a detector plane with samples on a focal spot plane may be determined. As illustrated in FIG. 9, both the detector plane and the focal spot plane may be quadrangles. On the detector plane, two points ($N_x=2$) may be sampled on a boundary in a direction $\vec{d_2}-\vec{d_1}$ (i.e., two first boundary points), and two points ($N_y=2$) may be sampled on a boundary in a direction $\vec{d_4}-\vec{d_1}$ (i.e., two first boundary points). On the focal spot plane, two points ($N_x=2$) may be sampled on a boundary in a direction $\vec{f_2}-\vec{f_1}$ (i.e., two second boundary points), and two points ($N_y=2$) may be sampled on a boundary in a direction $\vec{f_4}-\vec{f_1}$ (i.e., two second boundary points). The detector plane may include four boundary points $\vec{d_1}$, $\vec{d_2}$, $\vec{d_3}$, and $\vec{d_4}$. The focal spot plane may include four boundary points $\vec{f_1}$, $\vec{f_2}$, $\vec{f_3}$, and $\vec{f_4}$. Four lines $\mathcal{L}_{11}$, $\mathcal{L}_{21}$, $\mathcal{L}_{22}$, and $\mathcal{L}_{12}$ connecting the first boundary points with corresponding second boundary points may be determined. The line $\mathcal{L}_{11}$ may connect the first boundary point $\vec{d_1}$ with the second boundary point $\vec{f_1}$. The line $\mathcal{L}_{21}$ may connect the first boundary point $\vec{d_2}$ with the second boundary point $\vec{f_2}$. The line $\mathcal{L}_{22}$ may connect the first boundary point $\vec{d_3}$ with the second boundary point $\vec{f_3}$. The line $\mathcal{L}_{12}$ may connect the first boundary point $\vec{d_4}$ with the second boundary point $\vec{f_4}$. In some embodiments, each of the lines may be represented in the form of a set of points. Each set of points representing a line may be determined according to Formula (9):

$$\mathcal{L} = \{\vec{x} \mid \vec{x} = (1-t)\vec{f_{i,j}} + t\vec{d_{i,j}}, t > 0\}, \quad (9)$$

where $\mathcal{L}_{ij}$ denotes a line connecting a sample on the detector plane (also referred to as a detector sample or a detector point) $\vec{d_{i,j}}$ to a corresponding sample on the focal spot plane (also referred to as a focal spot sample or a focal spot point) $\vec{f_{i,j}}$, $\vec{x}$ denotes a point on the line $\mathcal{L}_{ij}$, and t parameterizes the set of points on the line $\mathcal{L}_{ij}$.

In 710, intersection points of the set of lines with voxel surfaces of the plurality of voxels may be determined. In some embodiments, a line connecting a sample on the detector plane with a sample on the focal spot plane may have one or more intersection points with the voxel surfaces. Merely for illustration purposes, a line $\mathcal{L} = \{\vec{x} \mid \vec{x} = (1-t)\vec{f} + t\vec{d}, t > 0\}$ connecting a first point $\vec{d} = (d_x, d_y, d_z)$ and a second $\vec{f} = (f_x, f_y, f_z)$ may intersect with a plane S at an intersection point. In some embodiments, the plane S may be represented as $x = x_s$ if the plane S is parallel to the y-z plane in the coordinate system 101. The coordinate of the intersection point may be determined according to Formula (10):

$$x = x_s, \; y = f_y + \frac{d_y - f_y}{d_x - f_x}(x_s - f_x), \quad (10)$$

$$z = f_z + \frac{d_y - f_y}{d_x - f_x}(x_s - f_x).$$

In some embodiments, all intersection points of the set of lines and the voxel surfaces of the plurality of voxels may be determined according to Formula (10). Merely for illustration purposes, intersection points of lines $\mathcal{L}_{ij}$ with voxel surfaces $S_{xk}$ may be represented by Equation (11):

$$(x_{ijk}, y_{ijk}, z_{ijk}) = \mathcal{L}_{ij} \cap S_{xk}, \quad (11)$$

where $(x_{ijk}, y_{ijk}, z_{ijk})$ denotes coordinates of the intersection points of lines $\mathcal{L}_{ij}$ with voxel surfaces $S_{xk}$. Intersection points of lines $\mathcal{L}_{ij}$ with voxel surfaces $S_{yl}$ may be represented by Equation (12):

$$(x_{ijl}, y_{ijl}, z_{ijl}) = \mathcal{L}_{ij} \cap S_{yl}, \tag{12}$$

where $(x_{ijl}, y_{ijl}, z_{ijl})$ denotes coordinates of the intersection points of lines $\mathcal{L}_{ij}$ with voxel surfaces $S_{yl}$. Intersection points of lines $\mathcal{L}_{ij}$ with voxel surfaces $S_{zn}$ may be represented by Equation (13):

$$(x_{ijn}, y_{ijn}, z_{ijn}) = \mathcal{L}_{ij} \cap S_{zn}, \tag{13}$$

where $(x_{ijn}, y_{ijn}, z_{ijn})$ denotes coordinates of the intersection points of lines $\mathcal{L}_{ij}$ with voxel surfaces $S_{zn}$. All determined intersection points may be represented by Equation (14):

$$Q \in (\mathcal{L}_{ij} \cap S_{xk}) \cup (\mathcal{L}_{ij} \cap S_{yl}) \cup (\mathcal{L}_{ij} \cap S_{zn}), \tag{14}$$

where Q denotes a determined intersection point.

In 712, the determined intersection points on each line may be ranked, so as to determine neighboring intersection points. Distances between two neighboring intersection points may be used to determine the forward projection model and/or the back projection model.

In some embodiments, a coordinate difference between a point on the detector plane and a corresponding point on the focal spot plane may be determined. Intersection points on a line connecting a sample on the detector plane with a corresponding sample on the focal spot plane may be ranked based on the coordinate difference. For instance, the coordinate difference may be determined by subtracting the coordinate of the first point from the coordinate of the second point. A determination may be made so as to whether an x-component of the coordinate difference is greater than a y-component of the coordinate difference. As used herein, an x-component of a coordinate difference is a component of the coordinate difference on the x direction. As used herein, a y-component of a coordinate difference is a component of the coordinate difference on the y direction. Based on the determination result, the intersection points on the line may be ranked. For instance, if the x-component of the coordinate difference is greater than the y-component of the coordinate difference, the intersection points on the line may be ranked according to x-components of the intersection points. As another example, if the x-component of the coordinate difference is smaller than the y-component of the coordinate difference, the intersection points on the line may be ranked according to y-components of the intersection points.

Merely for illustration purposes, for a line $\mathcal{L}_{ij}$, coordinate difference $\vec{f}_{i,J} - \vec{d}_{i,J}$ may be determined. A determination may be made so as to whether the x-component of the coordinate difference $\vec{f}_{i,J} - \vec{d}_{i,J}$ is greater than the y-component of the coordinate difference $\vec{f}_{i,J} - \vec{d}_{i,J}$. If the x-component of the coordinate difference $\vec{f}_{i,J} - \vec{d}_{i,J}$ is greater than the y-component of the coordinate difference $\vec{f}_{i,J} - \vec{d}_{i,J}$, the intersection points on the line $\mathcal{L}_{ij}$ may be ranked according to x-components of the intersection points. In some embodiments, the intersection points on the line $\mathcal{L}_{ij}$ may be ranked in an ascending order or descending order according to the x-components of the intersection points. If the y-component of the coordinate difference $\vec{f}_{i,J} - \vec{d}_{i,J}$ is greater than the x-component of the coordinate difference $\vec{f}_{i,J} - \vec{d}_{i,J}$, the intersection points on the line $\mathcal{L}_{ij}$ may be ranked according to y-components of the intersection points. In some embodiments, the intersection points on the line $\mathcal{L}_{ij}$ may be ranked in an ascending order or descending order according to the y-components of the intersection points. The ranked intersection points on the line $\mathcal{L}_{ij}$ may be represented as Equation (15):

$$P_n \in (\mathcal{L}_{ij} \cap S_{xk}) \cup (\mathcal{L}_{ij} \cap S_{yl}) \cup (\mathcal{L}_{ij} \cap S_{zn}), \tag{15}$$

where $P_n$ denotes the determined intersection points, and n may be an integer between 1 and N. N may be a total number (or count) of the determined intersection points.

In 714, the forward projection model and the back projection model may be determined based on the ranked intersection points on each line. In some embodiments, a voxel coordinate corresponding to each intersection point may be determined. As used herein, the voxel coordinate of a voxel refers to a coordinate of a center point of the voxel. Since a line passing through a voxel intersects with the voxel at two intersection points, the voxel coordinate may be determined based on the two intersection points. The two intersection points may be sequential intersection points on the line. As used herein, two intersection points are considered sequential if there are no other intersection points on the line that are located in between. The two intersection points may be referred to as two sequential intersection points corresponding to the voxel. In some embodiments, the voxel coordinate of the voxel corresponding to the two sequential intersection points may be determined based on coordinates of the two sequential intersection points. For example, the voxel coordinate corresponding to two sequential intersection point may be determined according to Formulas (16)-(18):

$$X_n = \text{floor}\left(\frac{(P_n|_x + P_{n+1}|_x)/2 + D_x}{d_x}\right) + 1, \tag{16}$$

$$Y_n = \text{floor}\left(\frac{(P_n|_y + P_{n+1}|_y)/2 + D_y}{d_y}\right) + 1, \tag{17}$$

$$Z_n = \text{floor}\left(\frac{(P_n|_z + P_{n+1}|_z)/2 + D_z}{d_z}\right) + 1, \tag{18}$$

where $X_n$ denotes x-component of the voxel coordinate corresponding to the intersection point $P_n$ and $P_{n+1}$, $Y_n$ denotes y-component of the voxel coordinate corresponding to the intersection point $P_n$ and $P_{n+1}$, $Z_n$ denotes z-component of the voxel coordinate corresponding to the intersection point $P_n$ and $P_{n+1}$, $P_n|_x$ denotes the x-component of the coordinate of the intersection point $P_n$, $P_n|_y$ denotes the y-component of the coordinate of the intersection point $P_n$, $P_n|_z$ denotes the z-component of the coordinate of the intersection point $P_n$, $P_{n+1}|_x$ denotes the x-component of the coordinate of the intersection point $P_{n+1}$, $P_{n+1}|_y$ denotes the y-component of the coordinate of the intersection point $P_{n+1}$, $P_{n+1}|_z$ denotes the z-component of the coordinate of the intersection point $P_{n+i}$, $(D_x, D_y, D_z)$ denotes a center of the plurality of voxels, floor (a) denotes a function that maps a real number a to a largest integer not greater than a, $d_x$, $d_y$ and, $d_z$ denote dimensions of the voxel on x axis, y axis, and z axis, respectively, n denotes an integer from 1 to N−1, and N is the number or count of the plurality of voxels.

In some embodiments, a norm of each two sequential intersection points of the ranked intersection points on the line may also be determined. The norm of two sequential intersection points may represent a distance between the two sequential intersection points.

In some embodiments, the contribution of the plurality of voxels on the line may be determined based on the voxel coordinate of the voxel corresponding to each of two sequential intersection points on the line and the difference norm of each two sequential intersection points on the line. For example, the contribution of the plurality of voxels on a line $\mathcal{L}_{ij}$ may be determined according to Formula (19):

$$S_{ij}=\Sigma_{n=1}^{N-1}(X_n,Y_n,Z_n)\cdot\|P_{n+1}-P_n\|, \quad (19)$$

where $S_{ij}$ denotes the contribution of the plurality of voxels on the line $\mathcal{L}_{ij}$, l represents an image value associated to the voxel with coordinates $(X_n, Y_n, Z_n)$, and $\|P_{n+1}-P_n\|$ denotes the absolute norm of two sequential intersection points $P_{n+1}$ and $P_n$.

In some embodiments, the forward projection model may be determined based on the contribution of the plurality of voxels on each line. Since there are a set of lines connecting points on the detector plane with points on the focal spot plane, a total contribution of the plurality of voxels to the set of lines may be determined with reference to Formula (19). The total contribution of the plurality of voxels on the set of lines may be determined by summing, regarding the set of lines, the contribution of the plurality of voxels on the each line, and averaging the total contribution by the count of the set of lines. Merely by ways of example, the total contribution of the plurality of voxels to the set of lines may be determined according to Formula (20):

$$S(f,d) = \frac{1}{N_x N_y}\Sigma_{i=1,j=1}^{N_x,N_y} S_{ij}, \quad (20)$$

where S(f,d) denotes the total contribution of the plurality of voxels to the set of lines (i.e., forward projection model).

In some embodiments, the contribution of a line on the plurality of voxels may be determined based on the difference norm of each two sequential intersection points of the ranked intersection points on the line. For example, the contribution of the line $\mathcal{L}_{ij}$ on the plurality of voxels may be determined according to Formula (21):

$$I_{ij}(X_n,Y_n,Z_n)=\Sigma_{n=1}^{N-1}\|P_{n+1}-P_n\|. \quad (21)$$

In some embodiments, the back projection model may be determined based on the contribution of each line on the plurality of voxels and the total contribution of the plurality of voxels to the set of lines. Since there are a set of lines connecting points on the detector plane with corresponding points on the focal spot plane, a total contribution of the set of lines on the plurality of voxels may be determined with reference to Formula (21). The total contribution of the set of lines on the plurality of voxels may be determined by summing, regarding the set of lines, the contribution of the each line on the plurality of voxels, and averaging the total contribution by the count of the set of lines. Merely by ways of example, the total contribution of the set of lines on the plurality of voxels may be determined according to Formula (22):

$$I = \frac{S(f,d)}{N_x N_y}\Sigma_{i=1,j=1}^{N_x,N_y} I_{ij}, \quad (22)$$

where I denote the total contribution of the set of lines on the plurality of voxels (i.e., back projection model).

It should be noted that the above description of the process 700 is provided for the purposes of illustration, not intended to limit the scope of the present disclosure. For persons having ordinary skills in the art, multiple variations and modifications may be reduced to practice in the light of the present disclosure. For example, the sizes of the focal spot plane, the detector plane, and/or the voxels may be set as variables, thus accommodating different imaging devices and/or application scenarios. As another example, the distance between the focal spot plane and the center of the voxels and/or the distance between the center of the voxels and the detector plane may also be set as variables, thus accommodating different imaging devices and/or application scenarios. However, these variations and modifications fall in the scope of the present disclosure.

Figure 10:
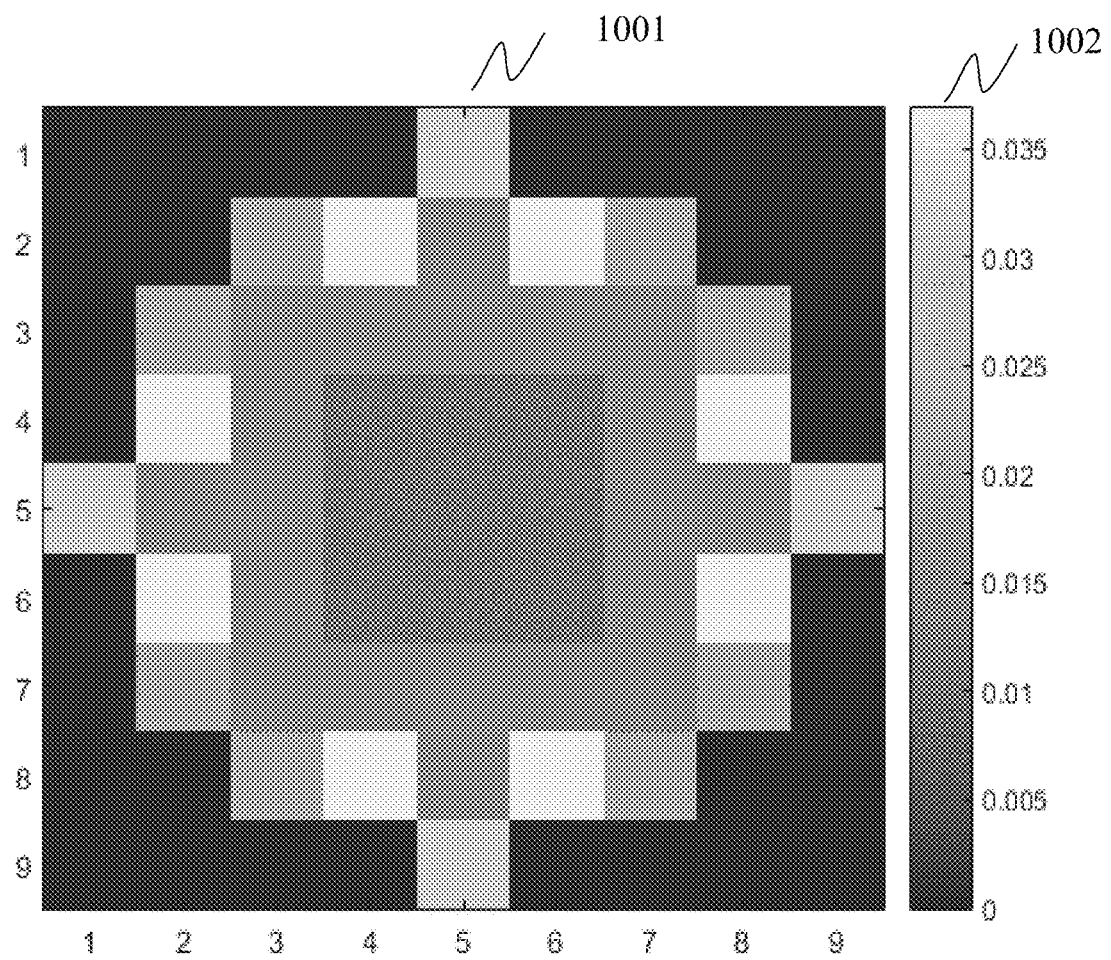
FIG. 10 is a schematic diagram illustrating a weighted focal spot plane according to some embodiments of the present disclosure.

FIG. 10 is a schematic diagram illustrating a weighted focal spot plane according to some embodiments of the present disclosure. When x-rays are emitting from a focal spot using, e.g., a high-intensity magnetic field, the x-rays on the focal spot may be unevenly distributed due to uneven tube current distribution (i.e., the density of the x-rays may vary at different parts of a focal spot plane 1001). The unevenly distributed x-rays may appear as cold and hot spots on the focal spot plane 1001. The weight corresponding to each part may be read out according to a scaleplate 1002 on a right side of the focal spot plane 1001.

In some embodiments, a weight representing the unevenly distributed x-rays may be determined for each part of the focal spot plane 1001. As illustrated in FIG. 10, ten second points may be sampled on each second boundary of the focal spot plane 1001 (i.e., ($N_x$=10, $N_y$=10). The focal spot plane 1001 may be meshed into 81 parts according to the ten second points sampled on each second boundary. Each part may correspond to a particular weight with it representing the temperature of the part. For the entire focal spot plane 1001, a sum of weights of the 81 parts (i.e., total weight) may be equal to 1. An optimized forward projection model considering the weight may be determined according to Formula (23):

$$S(f,d)=\Sigma_{i=1,j=1}^{N_x,N_y}w_{ij}\cdot S_{ij}. \quad (23)$$

An optimized back projection model considering the weight may be determined according to Formula (24):

$$I=S(f,d)\Sigma_{i=1,j=1}^{N_x,N_y}w_{ij}\cdot I_{ij}. \quad (24)$$

The optimized forward projection model and/or the optimized back projection model considering the weight may be used to reconstruct a CT image of a subject based on CT data of the subject in an iterative image reconstruction process.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method implemented on a computing apparatus having at least one processor and at least one computer-readable storage device, the method comprising:
acquiring computed tomography (CT) data, wherein the CT data is generated by scanning a subject using a CT scanner, the CT scanner including a focal spot and a detector, and the detector including a plurality of detector units;

obtaining a forward projection model and a back projection model, wherein the forward projection model and the back projection model are associated with sizes of the detector units and a size of the focal spot of the CT scanner; and reconstructing a CT image of the subject iteratively based on the CT data, the forward projection model, and the back projection model.

2. The method of claim 1, the obtaining a forward projection model and a back projection model including:

for each detector element of the plurality of detector elements, setting a detector plane representing the detector unit and a focal spot plane representing the focal spot in a three dimensional (3D) space;

setting a plurality of voxels representing the subject between the detector plane and the focal spot plane;

sampling a first count points on the detector plane and a second count of points on the focal spot plane;

determining a set of lines, each of the set of lines connecting a sampled detector point with a sampled focal spot point;

determining intersection points of the set of lines with surfaces of the plurality of voxels;

ranking the intersection points on each line; and determining, based on the ranked intersection points on each line, the forward projection model and the back projection model of the each line.

3. The method of claim 2, wherein the detector plane includes at least four first boundary points, and the focal spot plane includes at least four second boundary points.

4. The method of claim 3, the sampling a first count of first points on the detector plane and a second count of second points on the focal spot plane including:

determining boundaries of the detector plane and boundaries of the focal spot plane based on the at least four boundary points on each plane;

sampling a first portion of the first count of first points on the boundaries of the detector plane;

sampling a first portion of the second count of second points on the boundaries of the focal spot plane;

meshing the detector plane according to the first portion of first points;

meshing the focal spot plane according to the first portion of second points;

sampling a second portion of the first count of first points based on the meshed detector plane; and sampling a second portion of the second count of second points based on the meshed focal spot plane.

5. The method of claim 2, the ranking the determined intersection points on each line including:

determining a coordinate difference between a first point on the detector plane and a second point on the focal spot plane on the each line, the coordinate difference including an x-component and a y-component;

obtaining a determination result by determining whether the x-component is greater than the y-component; and ranking, based on the determination result, the intersection points on the each line.

6. The method of claim 5, wherein the determination result is that the x-component is greater than the y-component, and the ranking, based on the determination result, the intersection points including:

ranking the intersection points on the each line in an ascending order according to x-components of the intersection points.

7. The method of claim 5, wherein the determination result is that the x-component is smaller than the y-component, and the ranking, based on the determination result, the intersection points including:

ranking the determined intersection points on the each line in an ascending order according to y-components of the intersection points.

8. The method of claim 2, the determining the forward projection model based on the ranked intersection points on the each line including:

for each line,
determining an absolute norm of each two sequential intersection points of the ranked intersection points of the each line;

determining, based on coordinates of the each two sequential intersection points, a voxel coordinate of each voxel corresponding to the each two sequential intersection points;

determining first contribution of the plurality of voxels on the line based on the voxel coordinates and the absolute norms associated with the each line; and determining the forward projection model based on the first contribution of the plurality of voxels on the each line.

9. The method of claim 8, the determining the forward projection model based on the first contribution of the plurality of voxels on the each line including:

determining a total contribution by summing, regarding the set of lines, the first contribution of the plurality of voxels on the each line; and averaging the total contribution by the count of the set of lines.

10. The method of claim 8, the determining the back projection model based on the ranked intersection points including:

determining second contribution of each line on the plurality of voxels based on the absolute norms associated with the each line; and determining the back projection model based on the second contribution of each line on the plurality of voxels and the forward projection model.

11. A system, comprising:

at least one storage medium including a set of instructions; and at least one processor configured to communicate with the at least one storage medium, wherein when executing the set of instructions, the system is directed to perform operations including:

acquiring CT data, wherein the CT data is generated by scanning a subject using a CT scanner, the CT scanner including a focal spot and a detector, and the detector including a plurality of detector units;

obtaining a forward projection model and a back projection model, wherein the forward projection model and the back projection model are associated with sizes of the detector units and a size of the focal spot of the CT scanner; and reconstructing a CT image of the subject iteratively based on the CT data, the forward projection model, and the back projection model.

12. The system of claim 11, the obtaining a forward projection model and a back projection model including:

for each detector element of the plurality of detector elements, setting a detector plane representing the detector unit and a focal spot plane representing the focal spot in a three dimensional (3D) space;

setting a plurality of voxels representing the subject between the detector plane and the focal spot plane;

sampling a first count points on the detector plane and a second count of points on the focal spot plane;

determining a set of lines, each of the set of lines connecting a sampled detector point with a sampled focal spot point;

determining intersection points of the set of lines with surfaces of the plurality of voxels;

ranking the intersection points on each line; and determining, based on the ranked intersection points on each line, the forward projection model and the back projection model of the each line.

13. The system of claim 12, wherein the detector plane includes at least four first boundary points, and the focal plane includes at least four second boundary points.

14. The system of claim 13, the sampling a first count of first points on the detector plane and a second count of second points on the focal spot plane including:

determining boundaries of the detector plane and boundaries of the focal spot plane based on the at least four boundary points on each plane;

sampling a first portion of the first count of first points on the boundaries of the detector plane;

sampling a first portion of the second count of second points on the boundaries of the focal spot plane;

meshing the detector plane according to the first portion of first points;

meshing the focal spot plane according to the first portion of second points;

sampling a second portion of the first count of first points based on the meshed detector plane; and sampling a second portion of the second count of second points based on the meshed focal spot plane.

15. The system of claim 12, the ranking the determined intersection points on each line including:

determining a coordinate difference between a first point on the detector plane and a second point on the focal spot plane on the each line, the coordinate difference including an x-component and a y-component;

obtaining a determination result by determining whether the x-component is greater than the y-component; and ranking, based on the determination result, the intersection points on the each line.

16. The system of claim 15, wherein the determination result is that the x-component is greater than the y-component, and the ranking, based on the determination result, the intersection points including:

ranking the intersection points on the each line in an ascending order according to x-components of the intersection points.

17. The system of claim 15, wherein the determination result is that the x-component is smaller than the y-component, and the ranking, based on the determination result, the intersection points including:

ranking the determined intersection points on the each line in an ascending order according to y-components of the intersection points.

18. The system of claim 12, the determining the forward projection model based on the ranked intersection points on the each line including:

for each line, determining an absolute norm of each two sequential intersection points of the ranked intersection points of the each line;

determining, based on coordinates of the each two sequential intersection points, a voxel coordinate of each voxel corresponding to the each two sequential intersection points;

determining first contribution of the plurality of voxels on the line based on the voxel coordinates and the absolute norms associated with the each line; and determining the forward projection model based on the first contribution of the plurality of voxels on the each line.

19. The system of claim 18, the determining the forward projection model based on the first contribution of the plurality of voxels on the each line including:

determining a total contribution by summing, regarding the set of lines, the first contribution of the plurality of voxels on the each line; and averaging the total contribution by the count of the set of lines.

20. The system of claim 18, the determining the back projection model based on the ranked intersection points including:

determining second contribution of each line on the plurality of voxels based on the absolute norms associated with the each line; and determining the back projection model based on the second contribution of each line on the plurality of voxels and the forward projection model.

* * * * *